(12) United States Patent
Cohenford

(10) Patent No.: US 7,344,834 B2
(45) Date of Patent: Mar. 18, 2008

(54) METHOD FOR DNA AMPLIFICATION USING DNA BLOCKING PROBES

(75) Inventor: Menashi A. Cohenford, West Warwick, RI (US)

(73) Assignee: Cytyc Corporation, Marlborough, MA (US)

( * ) Notice: Subject to any disclaimer, the term of this patent is extended or adjusted under 35 U.S.C. 154(b) by 448 days.

(21) Appl. No.: 10/730,575

(22) Filed: Dec. 8, 2003

(65) Prior Publication Data

US 2005/0123934 A1   Jun. 9, 2005

(51) Int. Cl.
*C12Q 1/68* (2006.01)
*C12P 19/34* (2006.01)

(52) U.S. Cl. .......................................... 435/6; 435/91.2

(58) Field of Classification Search ...................... None
See application file for complete search history.

(56) References Cited

U.S. PATENT DOCUMENTS

| | | | | |
|---|---|---|---|---|
| 5,645,987 A | * | 7/1997 | Richards | 435/6 |
| 5,783,392 A | * | 7/1998 | Seibl et al. | 435/6 |
| 5,916,777 A | * | 6/1999 | Kacian et al. | 435/91.1 |
| 6,251,639 B1 | * | 6/2001 | Kurn | 435/91.2 |
| 6,893,819 B1 | * | 5/2005 | Sorge | 435/6 |

* cited by examiner

*Primary Examiner*—Young J. Kim
*Assistant Examiner*—Samuel Woolwine
(74) *Attorney, Agent, or Firm*—Theodore Allen; Mark J. Casey

(57) ABSTRACT

A process is disclosed for the amplification of a DNA template by subjecting a sample of biological material containing a target nucleotide sequence to amplification using a non-extendable oligonucleotide blocker. The method comprises using oligonucleotide primers and blockers to create primer extension products that are susceptible to cleavage by double-strand-specific ribonucleases. The continuous production and cycling of ribonuclease cleaved products allows for amplification of a target sequence.

15 Claims, 2 Drawing Sheets

● - Denotes ribonucleotide base at the 3' end terminus of the primer

∫ - Denotes cleavage by RNAse H after primer extension occurs

METHOD FOR DNA AMPLIFICATION USING DNA BLOCKING PROBES

BACKGROUND OF THE INVENTION

DNA amplification technology has developed rapidly in recent years as researchers have discovered its value for detection of nucleic acids that are present in small quantities in test samples. The use of probes is based upon the concept of complementarity. DNA has two strands bound together by hydrogen bonds between complementary nucleotides.

The DNA complex is normally stable, but the strands can be separated (or denatured) by conditions that disrupt the hydrogen bonding. The released single strands will reassociate only with another strand having a complementary sequence of nucleotides. This hybridization process can occur with both strands being in solution or with one of the strands being attached to a solid substrate.

A targeted nucleic acid sequence in an organism or cell may be only a very small portion of the entire DNA molecule so that it is very difficult to detect its presence using most labeled DNA probes. Much research has been carried out to find ways to detect only a few molecules of a targeted nucleic acid.

Such techniques, which generally involve the amplification and detection (and subsequent measurement) of minute amounts of target nucleic acids (either DNA or RNA) in a test sample, include inter alia the polymerase chain reaction (PCR) (Saiki, et al., Science 230:1350, 1985; Saiki et al., Science 239:487, 1988; PCR Technology, Henry A. Erlich, ed., Stockton Press, 1989; Patterson et al., Science 260:976, 1993), ligase chain reaction (LCR) (Barany, Proc. Natl. Acad. Sci. USA 88:189, 1991), strand displacement amplification (SDA) (Walker et al., Nucl. Acids Res. 20:1691, 1992), Q.beta. replicase amplification (Q.beta.RA) (Wu et al., Proc. Natl. Acad. Sci. USA 89:11769, 1992; Lomeli et al. Clin. Chem. 35:1826, 1989) and self-sustained replication (3SR) (Guatelli et al., Proc. Natl. Acad. Sci. USA 87:1874-1878, 1990).

The standard PCR method relies on two primers, one forward and one reverse. The combination of the two primers allows for the exponential amplification of particular DNA targets and a means for continuously generating DNA fragments of specific sizes. A major problem with PCR is having to continually denature DNA at 95 C, a situation that would cause the DNA polymerase to rapidly lose activity. In U.S. Pat. No. 5,849,497 (Steinman et.al.) a process is described for inhibiting the amplification of a DNA template by subjecting a sample of biological material containing nucleic acid to PCR using a DNA polymerase deficient in 5'exonuclease activity (i.e., Stoffel Taq polymerase).

The present invention describes a novel method of blocking DNA amplification, to allow for the amplification of DNA. The unique features of the present invention include: 1) the use of one primer instead of using two primers, 2) the use of a blocker DNA molecule to generate primer extension products of specified length, i.e., on the basis of the hybridization site of the non extendable oligonucleotide blocker on the DNA template relative to the up stream primer binding site, and 3) the use of a chimeric primer molecule comprising a sequence of deoxyribonucleotides with a 3' ribonucleotide terminus end to allow, in the presence of RNAse H, a continuous source of primer extension products of specific sizes.

Unlike other DNA amplifications methods which require multiple denaturation steps at 95 degrees Celsius, the method of the present invention requires denaturation of the DNA template at 95 degrees Celsius only once at the start of the procedure.

The utilization of chimeric primers to amplify nucleic acids or to obtain transcripts of a nucleic acid has been the subject of several patents and publications. Such a method is disclosed by the International Patent Application WO 00/56877 (Mukai et. al.) that describes using an endonuclease (RNAse H), a DNA polymerase enzyme and a chimeric oligonucleotide primer with a ribonucleotide on the 3' terminal end or on the 3' termination side to amplify DNA What distinguishes the Mukai et. al. method from the present invention is that in the Mukai procedure the method depends strictly on a DNA polymerase with a strand displacement activity. U.S. Pat. No. 5,744,308 (Guillou-Bonnici et. al.) describes an invention requiring a chimera oligonucleotide that can be used in a process for obtaining transcripts and/or amplification of a target sequence of a nucleic acid, having, at its 3' end, a downstream sequence. The oligonucleotide comprises successively, from 5' to 3', 1) a first oligonucleotide segment, of the DNA type, comprising a sense sequence of a promoter of an RNA polymerase, 2) a second oligonucleotide segment, of the DNA type, capable of hybridizing with the downstream sequence, and 3) a third oligonucleotide segment, of the RNA type, capable of hybridizing with a part of the target sequence contiguous to the downstream sequence, the third segment being blocked at 3'. A process using the chimera oligonucleotide and an enzyme system containing DNA polymerase activity, RNA polymerase activity, and a third activity, for example, an RNAse H activity provides transcription products of the target. By adding a second chimera oligonucleotide capable of hybridizing with the complement of the target, cyclic amplification of the target and its complement are obtained. The method of Guillou-Bonnici is different from the present invention by several aspects. First, the present invention has no need for an oligonucleotide segment, of the DNA type, comprising a sense sequence of a promoter of an RNA polymerase. Secondly, the method of Guillou-Bonnici et. al. was specifically tailored to amplify RNA and not DNA products.

U.S. Pat. Nos. 4,876,187 and 5,011,769 (Duck et. al. and Bekkaoui et. al.), disclose a cycling probe method that employs probes comprising RNA, preferably DNA: RNA: DNA chimeras.

Thus, there exists a need for an effective method to amplify DNA without the continuous thermocycling to high temperatures. The present invention satisfies this need and provides related advantages as well. The possible uses of the present invention, described above, are only examples and are not meant to limit the scope of the present invention in any way.

SUMMARY OF THE INVENTION

The present invention describes a means for amplifying DNA by a novel method. The method includes forming a nucleotide amplification reaction mixture comprising a DNA template; a single chimeric oligonucleotide primer consisting of a deoxyribonucleotide sequence with a ribonucleotide base at the 3' terminus that binds to said DNA template; a non-extendable oligonucleotide blocker that binds to said DNA template downstream from said primer; a DNA polymerase which lacks 5' exonuclease activity; a double-strand-specific ribonuclease, and appropriate buffers and nucleic acid precursors. The method also includes subjecting said nucleotide amplification reaction mixture to at least one thermocycle such that a first primer extension product is formed and cleaved at the ribonucleotide base releasing said first primer extension product. The method also includes hybridizing said first primer extension product to a first DNA triggering template comprising a target sequence, a first primer extension product binding site at the 3' terminus of said target sequence, and a contiguous second primer sequence which is conjoined to the 5' end of said target sequence by a ribonucleotide base.

The method includes subjecting said nucleotide amplification reaction mixture to at least one thermocycle such that a target amplification product is formed and said first DNA triggering template is cleaved at the ribonucleotide base releasing said second primer sequence with a ribonucleotide base at the 3' terminus. The method also includes hybridizing said second primer sequence to a second DNA triggering template which contains a second primer sequence binding site at the 3' terminus. The method also includes subjecting said nucleotide amplification reaction mixture to at least one thermocycle such that a third primer extension product is formed and cleaved at the ribonucleotide base releasing said third primer extension product, wherein said third primer extension product has the same nucleotide sequence as the first primer extension product Other features and advantages of the invention will be apparent from the following detailed description and claims.

DEFINITIONS

Figure 1:
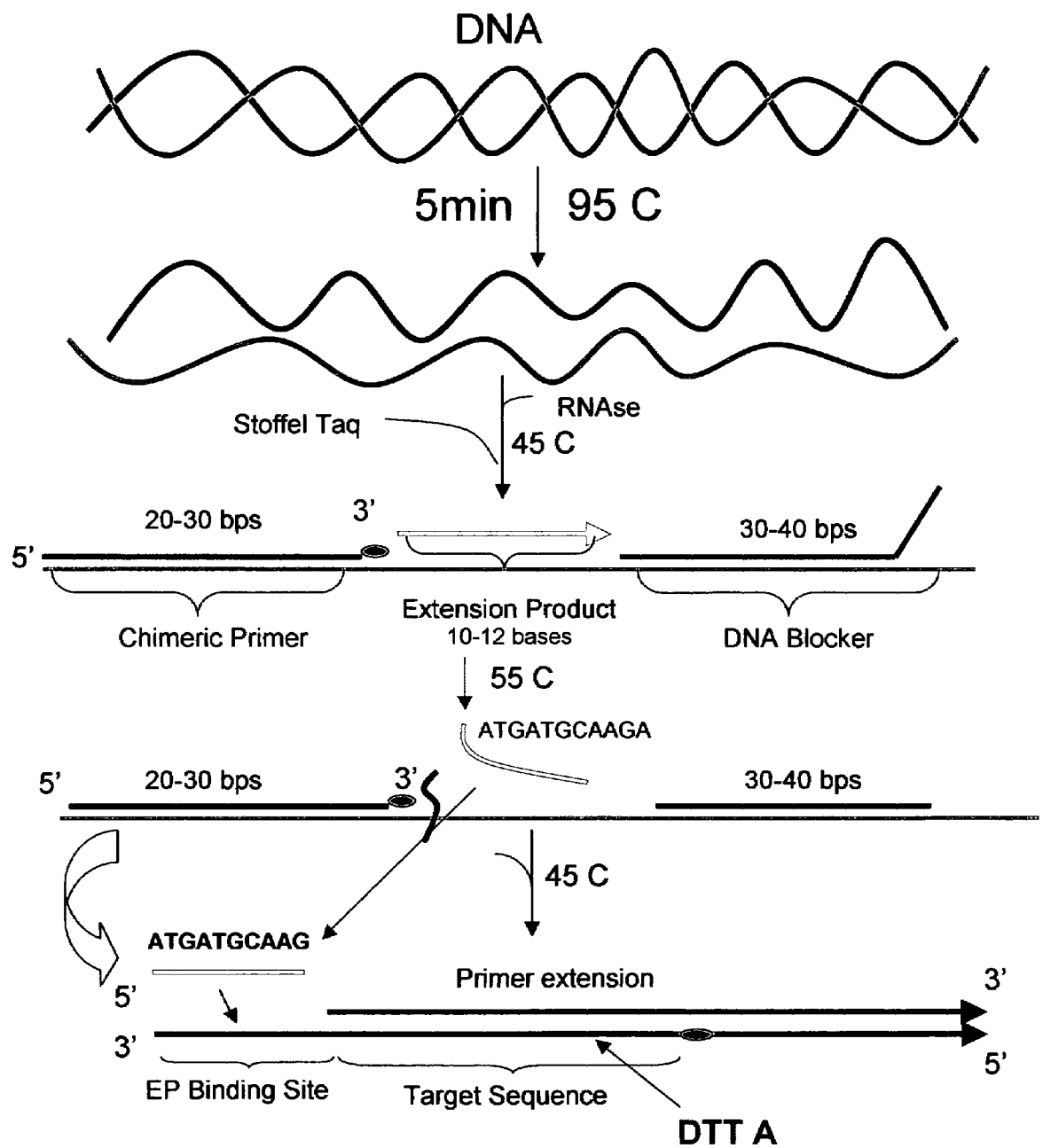
FIG. 1 is a schematic diagram illustrating an exemplary method for DNA amplification using DNA blocking probes.
Figure 1:
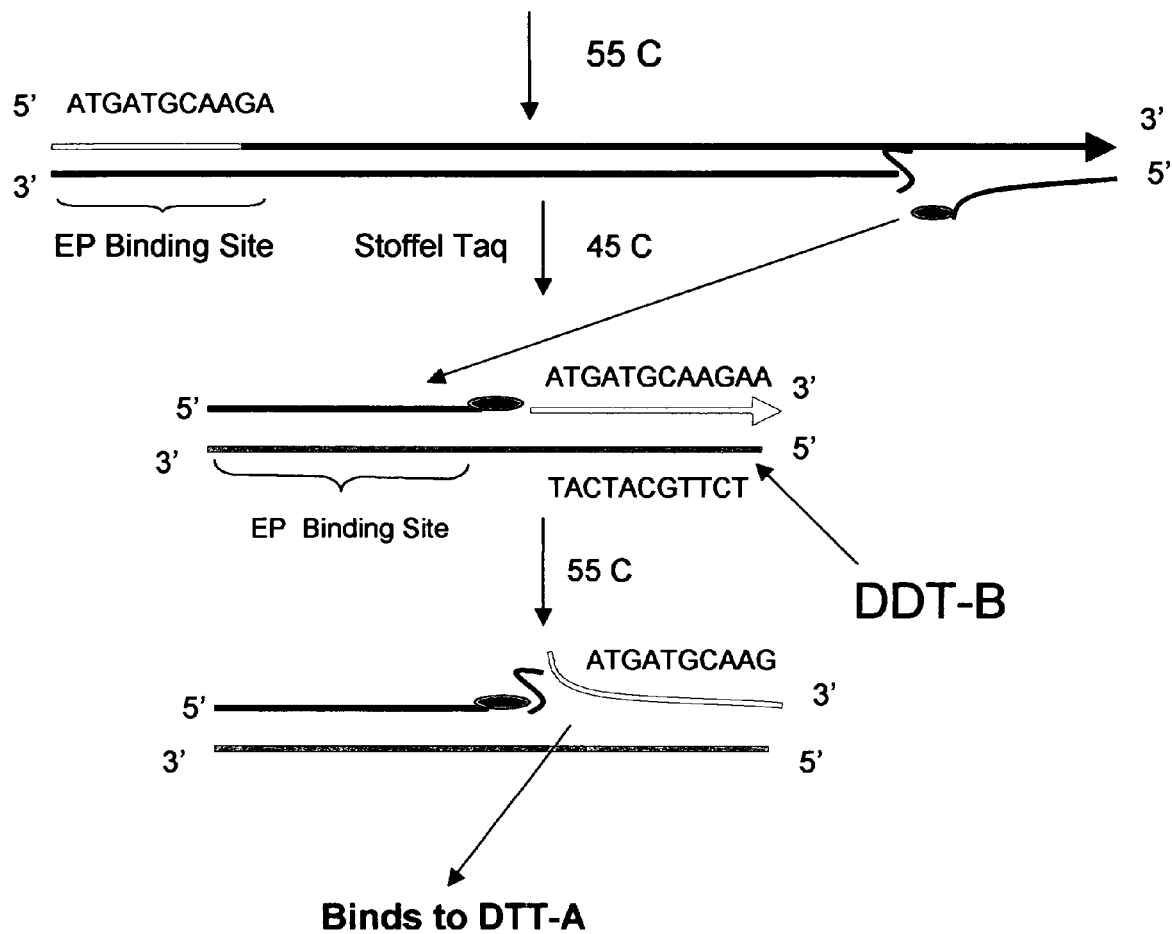

In the description that follows, a number of terms used in recombinant DNA technology are extensively utilized. In order to provide a clear and consistent understanding of the specification and claims, the following definitions are provided.

As used herein, the term "amplification" refers to any in vitro method for increasing the number of copies of a nucleic acid sequence with the use of a DNA polymerase. Nucleic acid amplification results in the incorporation of nucleotides into a DNA molecule or primer thereby forming a new DNA molecule complementary to a DNA template. The newly formed DNA molecule can be used a template to synthesize additional DNA molecules.

As used herein, the term "cleaving" means digesting the polynucleotide with enzymes or breaking the polynucleotide.

As used herein, the term "extension product" refers to a new DNA molecule complementary to the DNA template molecule formed by primer extension.

The term "non-extendable oligonucleotide blocker" refers to an oligonucleotide that is made non-extendable by adding bases to the 3' end that are not complementary to the target sequence and therefore do not base-pair and cannot be enzymatically extended.

As used herein, the term "nucleic acid or polynucleotide" refers to a linear sequence of covalently bond nucleotides. The nucleotides are either a linear sequence of polyribonucleotides or polydeoxyribonucleotides, or a mixture of both. Examples of nucleic acid in the context of the present invention include—single and double stranded DNA, single and double stranded RNA, and hybrid molecules that have mixtures of single and double stranded DNA and RNA.

Further, the nucleic acids of the present invention may have one or more modified nucleotides.

As used herein, the term "oligonucleotide" refers to a synthetic or natural molecule comprising a covalently linked sequence of nucleotides that are joined by a phosphodiester bond between the 3' position of the pentose of one nucleotide and the 5' position of the pentose of the adjacent nucleotide.

As used herein, the term "polymerase" refers to DNA polymerases, RNA polymerases and reverse transcriptases, which optimally perform nucleic acid chain elongation from 40 degrees Celsius to 80 degrees Celsius and more preferably from 55 degrees Celsius to 75 degrees Celsius. Thermostable polymerases as used herein have not necessarily be resistant against heat inactivation at temperatures above 60 degrees Celsius, but must retain a substantial portion of the full activity (>50%) at temperatures >55 degrees Celsius.

Thermostable DNA polymerases include, but are not limited to, DNA polymerases from thermophilic Eubacteria or Archaebacteria, for example, *Thermus aquaticus, T. thermophilus, T. bockianus, T. flavus, T. rubber, Thermococcus litoralis, Pyroccocus furiousus, P. wosei, Pyrococcus* spec. KGD, *Thermatoga maritime, Thermoplasma acidophilus*, and *Sulfolobus* spec. Preferable reverse transcriptases functional between 55-60 degrees Celsius includes, but are not limited to, MmLV reverse transcriptase, AMV reverse transcriptase, RSV reverse transcriptase, HIV-1 reverse transcriptase, and HIV-2 reverse transcriptase.

As used herein, the term "Polymerase Chain Reaction" or "PCR" means the application of cycles of denaturation, annealing with a primer and extension with a thermostable DNA polymerase, e.g. the Taq DNA polymerase, to amplify a target sequence of DNA The PCR process for amplifying nucleic acid is described in the documents U.S. Pat. Nos. 4,683,195 and 4,683,202.

As used herein, the term "primer" refer to single-stranded oligonucleotides that are complementary to sequence portions on a template nucleic acid molecule separated by a variable number of nucleotides. Covalent bonding of nucleotide monomers can extend primers annealed to the template nucleic acid during amplification or polymerization of a nucleic acid molecule catalyzed by the thermostable polymerases. Typically, primers are from 12 to 35 nucleotides in length and are preferably from 15 to 20 nucleotides in length. Primers are designed from known parts of the template, one complementary to each strand of the double strand of the template nucleic acid molecule, lying on opposite sides of the region to be synthesized. Primers can be designed and synthetically prepared as is well known in the art. Typically primers are used at concentrations of from 0.1 to 1 micromolar.

As used herein, the term "primer extension" refers to an in vitro method wherein a primer hybridized to an complementary sequence part of a single-stranded nucleic acid template molecule is extended by sequential covalent bonding of nucleotides to the 3' end of the primer forming a new DNA molecule complementary to the DNA template molecule. The primer extension method transforms a single-stranded nucleic acid template into a partially or completely double-stranded nucleic acid molecule. The primer extension method as used herein is a single step nucleic synthesis process without amplification of the copy number of the template nucleic acid molecule.

As used herein, the term "Stoffel fragment of Taq polymerase" is a known and commercially available DNA polymerase capable of adding nucleotides to the extending end of a primer, but lacking 5' exonuclease activity.

As used herein, the term "template" or "target sequence" refers to a double-stranded or single-stranded nucleic acid molecule, which serves a substrate for nucleic acid synthesis. In the case of a double-stranded DNA molecule, denaturation of its strands to form a first and a second strand is performed before these molecules may be used as substrates for nucleic acid synthesis. A primer, complementary to a portion of a single-stranded nucleic acid molecule serving as the template is hybridized under appropriate conditions and an appropriate polymerase may then synthesize a molecule complementary to the template or target sequence.

As used herein, the term "thermostable" refers to an enzyme that is resistant to inactivation by heat. The activity for a mesophilic enzyme may be inactivated by heat treatment. However, a thermostable enzyme does not mean to refer to an enzyme that is totally resistant to heat inactivation and thus heat treatment may reduce the 3' phosphatase activity to some extent. A thermostable enzyme typically will also have a higher optimum temperature than mesophilic enzyme.

This invention is further illustrated by the following examples that should not be construed as limiting. The contents of all references, patents and published patent applications cited throughout this application are incorporated herein by reference.

Other terms used in the fields of molecular and cell biology and the DNA recombination as used herein should be generally understood well by the person of ordinary skill in the applicable arts.

DETAILED DESCRIPTION OF THE INVENTION

The present invention includes a means for amplifying DNA by a novel method. The preferred embodiment of the method includes forming a nucleotide amplification reaction mixture comprising a DNA template containing a target nucleic acid sequence; a single chimeric oligonucleotide primer consisting of a deoxyribonucleotide sequence with a ribonucleotide base at the 3' terminus that binds to said DNA template; a non-extendable oligonucleotide blocker that binds to said DNA template downstream from said primer; a DNA polymerase which lacks 5' exonuclease activity; a double-strand-specific ribonuclease, and appropriate buffers and nucleic acid precursors. In a preferred embodiment, the DNA polymerase is the Stoffel fragment of Taq polymerase. In another preferred embodiment, the non-extendable oligonucleotide blocker is 30-40 base pairs in length and binds to a region of the DNA template 10 to 12 base pairs downstream from the single chimeric oligonucleotide primer that is 20 to 30 base pairs in length. In another embodiment, the double-strand-specific ribonuclease in RNaseH or any other endonuclease which cleaves at the ribose/deoxyribose nucleotide junction. Displacement of RNAse H cleaved products in the present invention occurs strictly by a thermocycling process, which involves adjusting the temperature of the nucleotide amplification mixture to exceed the Tm of the RNAse H cleaved oligonucleotide products.

An embodiment of the method also includes subjecting the nucleotide amplification reaction mixture to a change in temperature (e.g., 45 degrees Celsius) such that the non-extendable oligonucleotide blocker and the chimeric oligonucleotide primer bind to specific regions of the DNA template. After the binding of the primer and blocker, the DNA polymerase then fills in the gap between the primer and the blocker creating a first primer extension product.

Since the DNA polymerase used in the amplification mixture lacks 5' exonuclease and strand displacement activity, the DNA blocker prevents further extension of the first primer extension product. In a preferred embodiment, the first primer extension product is between 10 and 12 base pairs in length After extension, RNaseH cleaves the first primer extension product at the ribose/deoxyribose nucleotide junction. The amplification mixture is then raised to a temperature at which the first primer extension product is released (e.g., 55 degrees Celsius). In a preferred embodiment, the release of the extension product sequence from the DNA template occurs by adjusting the temperature of the amplification mixture to exceed the melting temperature of the primer/template hybrid.

The preferred embodiment of the method of the present invention also includes hybridizing the first primer extension product to a first DNA triggering template (DTT-A). The first DNA triggering template is comprised of two contiguous oligonucleotide sequences that are conjoined by a single ribonucleotide base. One oligonucleotide sequence is comprised of a target sequence and a first primer extension product binding site located at the 3' terminus of the target sequence. The second oligonucleotide comprises a contiguous second primer sequence that is conjoined to the 5' end of the target sequence by a ribonucleotide base. By adjusting the temperature of the nucleotide amplification reaction mixture (e.g., 45 degrees Celsius), the first primer extension product is allowed to bind to the 3' terminus of DTT-A Once the first primer extension product has hybridized to DTT-A, the DNA polymerase extends the primer over the entire DTT-A sequence, including the target sequence and the conjoining ribonucleotide base between the two contiguous oligonucleotide sequences. Primer extension over the ribonucleotide base makes it susceptible to RNAse H cleavage. Cleavage by RNAse H and an increase in temperature of the nucleotide amplification mixture (e.g., 55 degrees Celsius) releases a second primer sequence with a ribonucleotide base at the 3' terminus.

The preferred embodiment of the method of the present invention also includes hybridizing the second primer sequence to a second DNA triggering template (DTT-B). The second DNA triggering template contains a second primer sequence binding site at the 3' terminus as well as a nucleotide sequence that is complementary to the first primer extension product. By adjusting the temperature of the nucleotide amplification reaction mixture (e.g., 45 degrees Celsius), the second primer extension product is allowed to bind to the 3' terminus of DTT-B. Once the second primer extension product has hybridized to DTT-B, the DNA polymerase extends the primer to produce a third primer extension product. Primer extension from the 3' ribonucleotide base makes it susceptible to RNAse H cleavage. Cleavage by RNAse H and an increase in temperature of the nucleotide amplification mixture (e.g., 55 degrees Celsius) releases the third primer sequence that has a nucleotide sequence identical to the first primer extension product. Since the third primer extension product has the identical nucleotide sequence as does the first primer extension product, the third primer extension product may hybridize with DTT-A and the extension of DTT-A may be repeated. The continuous production and cycling of the third primer extension product allows for the amplification of the target DNA sequence.

The preferred embodiment of the method of the present invention also includes the detection of the amplified target DNA Conventional means, such as electrophoresis and ethidium bromide staining, may be used to detect the presence or absence of the amplified target DNA Also, DNA precursors may be labeled with a fluorescent dye, a chemiluminescent reagent, or a radioactive label such that incorporation of such precursors into primer extension products may be monitored. Other conventional means can also be used to detect the presence or absence of the amplified nucleic acid sequence, including but not limited to, detection by Southern blotting and the use of spectrometers.

The preferred embodiment of the method of the present invention also includes the Equivalents Those skilled in the art will recognize, or be able to ascertain using no more than routine experimentation, many equivalents to the specific embodiments of the invention described herein. Such equivalents are intended to be encompassed by the following claims.

lacks 5' exonuclease activity; and a double-strand-specific ribonuclease, and appropriate buffers and nucleic acid precursors;

b) subjecting said nucleotide amplification reaction mixture to at least one thermocycle such that a first primer extension product is formed and cleaved at the ribonucleotide base releasing said first primer extension product;

c) hybridizing said first primer extension product to a first DNA triggering template comprising a target sequence, a first primer extension product binding site at the 3' terminus of said target sequence, and a contiguous second primer sequence which is conjoined to the 5' end of said target sequence by a ribonucleotide base;

d) subjecting said nucleotide amplification reaction mixture to at least one thermocycle such that a target

What is claimed:

1. A method for amplifying a target nucleic acid sequence comprising the steps of;

a) forming a nucleotide amplification reaction mixture comprising a DNA template containing a target nucleic acid sequence; a single chimeric oligonucleotide primer consisting of a deoxyribonucleotide sequence with a ribonucleotide base at the 3' terminus that binds to said DNA template; a non-extendable oligonucleotide blocker that binds to said DNA template downstream from said primer; a DNA polymerase which amplification product is formed and said first DNA triggering template is cleaved at the ribonucleotide base releasing said second primer sequence with a ribonucleotide base at the 3' terminus;

e) hybridizing said second primer sequence to a second DNA triggering template which contains a second primer sequence binding site at the 3' terminus; and f) subjecting said nucleotide amplification reaction mixture to at least one thermocycle such that a third primer extension product is formed and cleaved at the ribonucleotide base releasing said third primer extension product, wherein said third primer extension product has the same nucleotide sequence as the first primer extension product.

2. The method of claim 1 wherein said DNA polymerase is the Stoffel1 fragment of Taq polymerase and has strand displacement activity.

3. The method of claim 1 wherein said double-strand-specific ribonuclease is thermostable RNaseH.

4. The method of claim 1 wherein said thermocycle includes a hybridization step at a temperature in the range of 30 to 50 degrees Celsius, a primer extension step at a temperature in the range of 50 to 70 degrees Celsius, and a double-strand-specific ribonuclease cleavage step at a temperature in the range of 50 to 70 degrees Celsius.

5. The method of claim 1 wherein said thermocycle is begun at a temperature in excess of 85 degrees Celsius.

6. The method of claim 1 wherein said nucleotide amplification reaction mixture is a polymerase chain reaction mixture.

7. The method of claim 1 wherein said nucleotide amplification reaction mixture includes a molar excess of said first and second DNA triggering templates over said DNA template.

8. A method for amplifying a target nucleic acid sequence comprising the steps of;
   a) forming a nucleotide amplification reaction mixture comprising a DNA template; a single chimeric oligonucleotide primer consisting of a deoxyribonucleotide sequence with a ribonucleotide base at the 3' terminus that binds to said DNA template; a non-extendable oligonucleotide blocker that binds to said DNA template downstream from said primer; a DNA polymerase which lacks 5' exonuclease and strand displacement activity; a double-strand-specific ribonuclease; and appropriate buffers and nucleic acid precursors
   b) subjecting said nucleotide amplification reaction mixture to at least one thermocycle such that a first primer extension product is formed and cleaved at the ribonucleotide base releasing said first primer extension product;
   c) hybridizing said first primer extension product to a first DNA triggering template comprising a target sequence, a first primer extension product binding site at the 3' terminus of said target sequence, and a contiguous second primer sequence which is conjoined to the 5' end of said target sequence by a ribonucleotide base;
   d) subjecting said nucleotide amplification reaction mixture to at least one thermocycle such that a target amplification product is formed and said first DNA triggering template is cleaved at the ribonucleotide base releasing said second primer sequence with a ribonucleotide base at the 3' terminus;
   e) hybridizing said second primer sequence to a second DNA triggering template which contains a second primer sequence binding site at the 3' terminus;
   f) subjecting said nucleotide amplification reaction mixture to at least one thermocycle such that a third primer extension product is formed and cleaved at the ribonucleotide base releasing said third primer extension product, wherein said third primer extension product has the same nucleotide sequence as the first primer extension product;
   g) repeating steps c)-f); and
   h) detecting amplification of said target sequence.

9. The method of claim 8 wherein said DNA polymerase is the Stoffel1 fragment of Taq polymerase.

10. The method of claim 8 wherein said double-strand-specific ribonuclease is a thermostable RNaseH.

11. The method of claim 8 wherein said thermocycle includes a hybridization step at a temperature in the range of 30 to 50 degrees Celsius, a primer extension step at a temperature in the range of 50 to 70 degrees Celsius, and a double-strand-specific ribonuclease cleavage step at a temperature in the range of 50 to 70 degrees Celsius.

12. The method of claim 8 wherein said thermocycle is begun at a temperature in excess of 85 degrees Celsius.

13. The method of claim 8 wherein said nucleotide amplification reaction mixture is a polymerase chain reaction mixture.

14. The method of claim 8 wherein said target product in step d) is labeled with a detectable marker and said labeled target product is detected in step h).

15. The method of claim 8 wherein said nucleotide amplification reaction mixture includes a molar excess of said first and second DNA triggering templates over said DNA template.

* * * * *

```
                        SEQUENCE LISTING

<160> NUMBER OF SEQ ID NOS: 3

<210> SEQ ID NO 1
<211> LENGTH: 11
<212> TYPE: DNA
<213> ORGANISM: Artificial
<220> FEATURE:
<223> OTHER INFORMATION: Artifical sequence used for probe

<400> SEQUENCE: 1
atgatgcaag a                                                           11

<210> SEQ ID NO 2
<211> LENGTH: 10
<212> TYPE: DNA
<213> ORGANISM: Artificial
<220> FEATURE:
<223> OTHER INFORMATION: Artifical sequence used as probe

<400> SEQUENCE: 2
atgatgcaag                                                             10

<210> SEQ ID NO 3
<211> LENGTH: 11
<212> TYPE: DNA
<213> ORGANISM: Artificial
<220> FEATURE:
<223> OTHER INFORMATION: Artifical sequence for probe

<400> SEQUENCE: 3
tactacgttc t                                                           11
```